United States Patent
Schindler et al.

(10) Patent No.: US 6,500,631 B1
(45) Date of Patent: Dec. 31, 2002

(54) METHOD FOR DETECTING OXIDIZED FORMS OF SOLUBLE GUANYLATE CYCLASE

(75) Inventors: Ursula Schindler, Bad Soden (DE); Hartmut Strobel, Liederbach (DE); Peter Schindler, Bad Soden (DE); Alexander Muelsch, Heidelberg (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/661,915

(22) Filed: Sep. 14, 2000

(30) Foreign Application Priority Data

Sep. 15, 1999 (DE) .................................. 199 44 226

(51) Int. Cl.[7] .............................................. C12Q 1/48
(52) U.S. Cl. ...................................... 435/15; 435/21
(58) Field of Search ................................. 435/15, 21

(56) References Cited

U.S. PATENT DOCUMENTS 5,618,665 A     4/1997   Lurie et al.
6,335,334 B1 *   1/2002   Schindler et al. ......... 514/231.5

FOREIGN PATENT DOCUMENTS

| DE | 198 37 015 | 2/2000 |
|----|------------|--------|
| SU | 876715 | 10/1981 |
| WO | WO 00/02851 | 1/2000 |

OTHER PUBLICATIONS

Schrammel A. Characterization of 1H–[1,2,4]Oxadiazolo[4,3–a]quinoxalin–1–one as a Heme Site Inhibitor of Nitric Oxide Sensitive Guanylyl Cyclase. Molecular Pharmacology 50(1–5)1996, 1–5.*
Stone J. Spectral and Ligand Binding Properties of an Unusual Hemoprotein, The Ferric Form of Soluble Guanylate Cyclase. Biochemistry 1996 35(10)3258–3262.*
Foerster, John; Harteneck, Christian; Malkewitz, Jürgen; Schultz, Günter; and Koesling, Doris, "A functional heme–binding site of soluble guanylyl cyclase requires intact N–termini of $\alpha_1$ and $\beta_1$ subunits," *Eur. J. Biochem.*, 240:380–386 (1996).
Giuili, Galicia; Scholl, Ute; Bulle, Frédérique; and Guellaën, Georges, "Molecular clonging of the cDNAs coding for the two subunits of soluble guanylyl cyclase from human brain," *FEBS LETTERS*, 304(1):83–88 (Jun. 1992).
Humbert, Peter; Niroomand, Feraydoon; Fischer, Gabriela; Mayer, Bernd; Koesling, Doris; Hinsch, Klaus–Dieter; Schultz, Günter; and Böhme, Eycke, "Preparation of Soluble Guanylyl Cyclase from Bovine Lung by Immunoaffinity Chromatography," *Methods in Enzymology*, 195:384–391 (1991).
Ignarro, Louis J., "Regulation of Cytosolic Guanylyl Cyclase by Porphyrins and Metalloporphyrins," *Advances in Pharmacology*, 26:35–65 (1994).
Koesling, D. and Friebe, A., "Soluble Guanylyl Cyclase: Structure and Regulation," *Reviews of Physiology Biochemistry and Pharmacology*, 135:42–64 (1999).

Moro, María A.; Russell, Rachel J.; Cellek, Selim; Lizasoain, Ignacio; Su, Yunchao; Darley–Usmar, Victor M.; Radomski, Marek W.; and Moncada, Salvador, "cGMP mediates the vascular and platelet actions of nitric oxide: Confirmation using an inhibitor of the soluble guanylyl cyclase," *Proc. Natl. Acad. Sci. USA*, 93:1480–1485 (Feb. 1996).
Nakane, Masaki; Arai, Kazuko; Saheki, Shuichi; Kuno, Takayoshi; Buechler, Wolfgang; and Murad, Ferid, "Molecular Cloning and Expression of cDNAs Coding for Soluble Guanylate Cyclase from Rat Lung," *J. of Biological Chemistry*, 265(28):16841–16845 (Oct. 5, 1990).
Schrammel, Astrid; Behrends, Sönke; Schmidt, Kurt; Koesling, Doris; and Mayer, Bernd, "Characterization of 1H–[1,2,4]Oxadiazolo[4,3–a]quinoxalin–1–one as a Heme–Site Inhibitor of Nitric Oxide–Sensitive Guanylyl Cyclase," *Molecular Pharmacology*, 50:1–5 (1996).
Vesely, D. L., "B complex vitamins activate rat guanylate cyclase and increase cyclic GMP levels," *European Journal of Clinical Investigation*, 15:258–262 (1985).
Yuen, Peter S. T.; Potter, Lincoln R.; and Garbers, David L., "A New Form of Guanylyl Cyclase is Preferentially Expressed in Rat Kidney," *Biochemistry*, 29:10872–10878 (1990).
Olesen et al., "Characterization of NS 2028 as a Specific Inhibitor of Soluble Guanylyl Cyclase", British Journal of Pharmacology, vol. 123, pp. 299–309 (1998).
Ignarro et al., "Selective Alterations in Responsiveness of Guanylate Cyclase to Activation by Nitroso Compounds during Enzyme Purification", Biochemica et Biophysica Acta, vol. 673, pp. 394–407 (1981).
Gupte et al., "NADPH and Heme Redox Modulate Pulmonary Artery Relaxation and Guanylate Cyclase Activation by NO", Am. J. Physiol., vol. 277, pp. L1124–L1132 (1999).
Schrammel et al., "Characterization of 1H–[1,2,4]Oxadiazolo[4,3–a]quinoxalin–1–one as a Heme–Site Inhibitor of Nitric Oxide–Sensitive Guanylyl Cyclase", Molecular Pharmacology, vol. 50, pp. 1–5 (1996).
Makino et al., "EPR Characterization of Axial Bond in Metal Center of Native and Cobalt–substituted Guanylate Cyclase", The Journal of Biological Chemistry, vol. 274, No. 12, Issue of Mar. 19, pp. 7714–7723 (1999).
European Search Report of Apr. 20, 2001.
Derwent Abstract of DE 198 37 015.

\* cited by examiner

*Primary Examiner*—Ralph Gitomer
(74) *Attorney, Agent, or Firm*—Finnegan, Henderson, Farabow, Garrett & Dunner, LLP

(57) ABSTRACT

The invention relates to methods for detecting a soluble guanylate cyclase whose heme iron is in the trivalent oxidation state, and to methods for finding chemical substances which stimulate the activity of a soluble guanylate cyclase when the heme iron of at least part of this soluble guanylate cyclase is oxidized to the trivalent state and also to diagnostic aids or kits for detecting a soluble guanylate cyclase with trivalent heme iron. Further, the invention relates methods for detecting a soluble guanylate cyclase lacking a heme group, and to methods for finding chemical substances which stimulate the activity of a soluble guanylate cyclase lacking a heme group.

12 Claims, No Drawings

METHOD FOR DETECTING OXIDIZED FORMS OF SOLUBLE GUANYLATE CYCLASE

The invention relates to methods for detecting soluble guanylate cyclase whose heme-complexed iron is oxidized or which contains no heme group, to screening methods for identifying compounds able to activate soluble guanylate cyclase with oxidized heme iron, and to diagnostic aids for detecting a soluble guanylate cyclase having a trivalent heme iron.

Soluble guanylate cyclases are heterodimeric proteins. They consist in each case of an α subunit and a β subunit, and contain heme as a prosthetic group. Binding of the signal molecule nitric oxide ("NO") to the heme group activates the enzyme. The cGMP formed through the enzymatic activity of soluble guanylate cyclase is involved, inter alia, in the activation of cGMP-dependent protein kinases and in the regulation of phosphodiesterases or of ion channels. Four isoforms of the subunits have been described. These differ in their sequence and in their tissue-specific and development-specific expression. Subtypes $\alpha_1$ and $\beta_1$ are found mainly in lung, kidney and brain. The $\beta_2$ chain is expressed mainly in liver and kidney, and the $\alpha_2$ subunit is expressed mainly in placenta. Dimerization of the subunits is a precondition for a catalytically active soluble guanylate cyclase. The heterodimers $\alpha_1/\beta_1$, $\alpha_2/\beta_1$, and $\alpha_1/\beta_2$ are known. The region of the catalytic domain in all the subunits shows a high degree of homology.

Soluble guanylate cyclase (sGC) contains one heme group per heterodimer. Binding of the heme takes place via His-105 in the $\beta_1$ chain. Mutants no longer containing His-105 in the N terminus of the $\beta_1$ subunit cannot be stimulated by NO. The heme group in soluble guanylate cyclase consists of an organic part of the molecule and an iron atom. The organic part, protoporphyrin IX, contains four pyrrole rings which are linked by methine bridges to form a tetrapyrrole system. The iron atom in the heme group is bound to four nitrogen atoms in the center of the protoporphyrin ring. In addition, it is able to engage in two other linkages. The oxidation state of the iron in the heme may be +2 (ferrous form) or +3 (ferric form; oxidized form). The oxidation state of the heme group iron has a crucial effect on the enzymatic function of soluble guanylate cyclase. The enzyme with a trivalent form heme iron shows only basal enzymatic activity, like a soluble guanylate cyclase without a heme group, and cannot be stimulated by NO. The preparation of a heme-free soluble guanylate cyclase is described in Eur. J. Biochem. 240, 380–386 (1996).

Soluble guanylate cyclase (sGC) catalyzes the conversion of GTP into cyclic guanosine monophosphate (cGMP) and pyrophosphate. cGMP acts as an intracellular messenger (second messenger). Second messengers are produced inside the cell in cascade-like reactions. Their level is controlled by extracellular signals such as hormones, neurotransmitters, growth factors, odorous substances, peptides, or light. Formation of second messengers serves to enhance signals. The second messenger transmits signals inside the cell to particular target proteins (kinases, phosphatases, ion channels, and others) which depend on the cell type. Modulation of soluble guanylate cyclase therefore leads, via the influence on the cGMP levels and target proteins controlled thereby, to a number of pharmacological effects. Examples of mechanisms influenced in this way are the relaxation of smooth muscles (for example, in the walls of blood vessels), the inhibition of platelet activation, the inhibition of proliferation of smooth muscle cells, and the adhesion of leukocytes.

Soluble guanylate cyclase is detectable in organs such as, for example, the heart, lung, liver, kidney, and brain of all mammals, including humans. In pathological processes or in processes relevant for pathological events, the oxidation state of the heme group iron in soluble guanylate cyclase may play an essential part. A higher proportion of soluble guanylate cyclase with oxidized heme group iron would result in the possibility of diminishing activation of soluble guanylate cyclase by endogenous NO. This might lead, inter alia, to an increase in blood pressure, activation of platelets, increased proliferation of cells or enhanced adhesion of cells to permanent high blood pressure, stable or unstable angina pectoris, thromboses, myocardial infarct, strokes, pulmonary edemas, erectile dysfunction, uncontrolled tissue growth with tumor formation, diabetes, renal dysfunction, hepatic dysfunctions, or vascular dysfunction. The endothelial cells of vessel walls secrete NO as paracrine hormone inter alia for activating soluble guanylate cyclase. Compounds frequently used for pharmacological stimulation of soluble guanylate cyclase act as NO donors via intermediate NO release. Examples of NO donors are the organic nitrates. In addition, various compounds which do not act via NO release, but which modify the activity of soluble guanylate cyclase, have been described.

Activation of soluble guanylate cyclase by NO donors or free NO takes place exclusively in the reduced, i.e., ($Fe^{2+}$)-containing, state of heme iron. This is evident from experiments carried out by A. Schrammel et al. in Mol. Pharmacol. 50, 1 (1996) with 1H-[1,2,4]oxadiazolo[4,3-a]quinoxalin-1-one ("ODQ"). ODQ is a specific and highly effective inhibitor of soluble guanylate cyclase. ODQ interacts with the prosthetic heme group. In vitro, the substance causes irreversible oxidation of the heme iron of soluble guanylate cyclase. Treatment of soluble guanylate cyclase with ODQ results in the stimulating effect of NO on the enzyme being lost. Oxidation of the heme iron in soluble guanylate cyclase can also be brought about with oxadiazolo(3,4-d)benz(b)(1,4)oxazin-1-one (Olesen et al., British Journal of Pharmacology 123, 299–309 (1998)) or potassium ferricyanide (Koesling et al., in "Reviews of Physiology Biochemistry and Pharmacology," pp. 41–65, Springer Verlag (1999)). There are also activators of soluble guanylate cyclase which do not act via NO release. A description thereof has been given by, for example, Vesely et al. in Eur. J. Clin. Invest. 15, 258 (1985). Stimulation of heme-free soluble guanylate cyclase by protoporphyrin IX has been demonstrated by Ignarro et al. in Adv. Pharmacol 26, 35 (1994). The effect of protoporphyrin IX cannot be inhibited by ODQ, but is instead enhanced (Koesling and Friebe, Physiol. Biochem. Pharmacol. 135, 41 (1999)). The activators disclosed to date for soluble guanylate cyclase stimulate the enzymatic activity thereof only if the heme iron is in the reduced, i.e. $Fe^{2+}$-containing, state.

Recently, another class of chemical compounds has been described (WO 00/02851), the sulfur-substituted sulfonylamino carboxylic acid N-arylamides, whose representatives are able to activate soluble guanylate cyclase.

The activity of soluble guanylate cyclase to date has been detected by enzymatic methods for detecting cGMP and cAMP, or by photometric methods for detecting the heme group. However, for establishing the dependence of a condition with a pathological change on the state of soluble guanylate cyclase, it is insufficient merely to detect the protein by immunological detection methods or by labeling techniques. It is just as important to know the redox state of the complexed iron in the heme group. Until now, it has only been possible to find information about the functionality of the heme in soluble guanylate cyclase by determining the redox state of the complexed heme iron by ESR measurements or by photometry. These determinations have the disadvantage that they depend on the availability of technically complex equipment. Moreover, the methods have only limited suitability for specific measurements because impurities from other heme-containing proteins readily interfere.

One object of the present invention was therefore to provide simplified and specific methods for detecting an oxidation state of soluble guanylate cyclase. Another object of the invention was to provide methods for finding a chemical substance which activates soluble guanylate cyclase when its heme iron is oxidized to the trivalent state. The invention also relates to diagnostic aids which are suitable for identifying soluble guanylate cyclases whose heme iron is oxidized in the trivalent state.

The present invention relates to a method for detecting a soluble guanylate cyclase where the iron of the heme in this soluble guanylate cyclase is in the trivalent oxidation state, and where the method comprises the following steps:

a) provision of a soluble guanylate cyclase;

b) provision of at least one chemical compound which stimulates the activity of a soluble guanylate cyclase when the iron of the heme in this soluble guanylate cyclase is in the trivalent oxidation state;

c) incubation of a soluble guanylate cyclase provided as in a) with a chemical compound provided as in b);

d) determination of the activity of soluble guanylate cyclase after incubation as in c).

Specifically, the invention relates to a method for detecting soluble guanylate cyclase having a heme group with iron in a trivalent oxidation state, comprising:

a) incubating a sample of soluble guanylate cyclase having a known activity with a chemical compound which stimulates activity of soluble guanylate cyclase having a heme group with iron in the trivalent oxidation state;

b) measuring the activity of the soluble guanylate cyclase after incubation; and c) comparing the activity of the soluble guanylate cyclase after incubation with the activity before incubation, wherein an increase in activity indicates the presence of soluble guanylate cyclase having a heme group with iron in the trivalent oxidation state.

The soluble guanylate cyclase may consist of a mixture of molecules of soluble guanylate cyclase, with not all the soluble guanylate cyclase molecules being present with a heme iron in the trivalent oxidation state. In particular, some of the heme groups of the soluble guanylate cyclase molecules can be in the trivalent oxidation state and some others in the divalent oxidation state, to result in a mixture with varying proportions of the oxidation states of the heme iron. The method for detecting a soluble guanylate cyclase whose heme iron is in the trivalent form can be carried out by comparison with reference values. The reference values may be obtained inter alia from experiments in which the dependence of the activity of soluble guanylate cyclase on known proportions of soluble guanylate cyclase with trivalent heme iron has been determined. A measure of the particular proportion of soluble guanylate cyclase with trivalent heme iron can be obtained by pretreatment of the soluble guanylate cyclase with ODQ and subsequent determination of the activity of this soluble guanylate cyclase. The determined reference values can then be used as calibration plots for quantitative determinations of soluble guanylate cyclase with heme iron in the trivalent oxidation state.

The soluble guanylate cyclase can be used in various states, for example as diverse heterodimeric soluble guanylate cyclase. It is possible in principle to employ a soluble guanylate cyclase from any species, in particular, from any mammalian species. Soluble guanylate cyclase from cattle is preferably used, and is preferably isolated from pulmonary tissue. Human soluble guanylate cyclase is particularly preferably used. The provided soluble guanylate cyclase can preferably be composed in each case of an $\alpha$ subunit, for example of the $\alpha_1$ or $\alpha_2$ subunit, and of a $\beta$ subunit, for example of the $\beta_1$ or $\beta_2$ subunit. It is possible and preferable for subunits of the soluble guanylate cyclase to be used for the method of the present invention. Corresponding sequence information is indicated in Giuili et al. (*FEBS Letters* 304, 83–88 (1992)) for the two subunits of soluble guanylate cyclase originally isolated from human brain, or in Nakane et al. (*Journal of Biol. Chem.* 265, 16841–16845 (1990)) for cDNAs of the soluble guanylate cyclase from rat lung tissue, or in Yuen et al. (*Biochemistry* 29, 10872–10878 (1990)) for a soluble guanylate cyclase from rat kidneys.

The provision of a soluble guanylate cyclase can take place by isolation from a biological material using biochemical methods. In such cases in particular there is frequently a mixture of soluble guanylate cyclase molecules with different oxidation states of the heme iron. Biochemical methods may be, inter alia: methods for disintegrating the biological material, centrifugation, chromatographic separations, gel electrophoreses, isoelectric focusing, and immunological methods. Biological material may comprise eukaryotic cells or prokaryotic cells, disintegrates of the cells or preparations from disintegrates of the cells, whole cells or parts or fractions of the cells. The eukaryotic cells include inter alia, for example, cells from tissues or organs such as heart, blood vessels, lung, blood, brain, liver, kidney, adipose tissue, muscle from vertebrates including humans, tissue or blood samples, but also cells from human or animal cell cultures, and insect cell cultures. Specific examples are platelets, which can be obtained from human or animal blood samples, and smooth muscle cells, which can be isolated, for example, from blood vessels of animal or human origin. Further examples are biopsy material, organs and tissues and parts thereof left over after transplantations, umbilical cords or placentae. Prokaryotic cells may be, for example, bacteria, including *Escherichia coli, Salmonella typhimurium,* or *Bacillus subtilis,* as well as fungi such as *Saccharomyces cerevisiae, Saccharomyces pombe* or *Pichia pastoris.* In a particular embodiment of the invention, the soluble guanylate cyclase can be recombinant material prepared, for example, by expression in eukaryotic or prokaryotic cells, in which case the soluble guanylate cyclase, with or without a prosthetic heme group, is accumulated within the cells or excreted into the medium, using expression vectors. In a specific embodiment, the soluble guanylate cyclase is isolated by a method as described by Humbert P. et al. in *Methods of Enzymology* 195, 384–391 (1991).

One embodiment provides a soluble guanylate cyclase which has been treated with an oxidizing agent. Another embodiment provides a soluble guanylate cyclase which has been treated with ODQ. The concentration of ODQ is, for example, from 0.001 mM to 0.5 mM, preferably 0.005 mM to 0.1 mM and, particularly preferably, 0.01 mM. It may also be preferred to provide a soluble guanylate cyclase which has been treated with oxadiazolo(3,4-d)benz(b)(1,4)oxazin-1-one or another derivative of ODQ. In another preferred embodiment, a soluble guanylate cyclase which has been treated with potassium ferricyanide is provided. The treatment of the soluble guanylate cyclase with oxidizing agents and/or ODQ and/or other compounds may cause oxidation of the heme iron, i.e., conversion of the iron from the divalent oxidation state ($Fe^{2+}$) into the trivalent oxidation state ($Fe^{2+}$). Depending on the chosen conditions, the conversion may affect only some or, in particular embodiments, all the treated soluble guanylate cyclase molecules. The method of the present invention comprises using a form of soluble guanylate cyclase in which the heme iron is in the trivalent oxidation state either for only some of the soluble guanylate cyclase molecules or, in a preferred embodiment, in all of the soluble guanylate cyclase molecules.

The provision of the soluble guanylate cyclase comprises the preparation of suitable forms for incubation with selected chemical compounds, where incubation means that the soluble guanylate cyclase and the chemical compound are brought into contact with one another. The protein can be suspended or dissolved, for example, in aqueous solvents supplemented by buffers, ions, or else auxiliary reagents. It may also, for example, be attached to carrier material and used, immobilized in this form, suspended in solvents.

Chemical compounds which can be provided to stimulate the activity of soluble guanylate cyclase with trivalent heme iron may be either individual chemical compounds or may be combinations of chemical compounds. The chemical compounds can be, for example, synthesized or isolated from natural substances. It is possible in principle to use for the provision all chemical compounds which stimulate the activity of a soluble guanylate cyclase when the iron of the heme of this soluble guanylate cyclase is in the trivalent oxidation state.

To carry out the method for detecting soluble guanylate cyclase with a heme iron in the trivalent oxidation state it is possible to use, for example, the chemical compound 2-(4-chlorophenylsulfonylamino)-4,5-dimethoxy-N-(4-(thiomorpholine-4-sulfonyl)phenyl)benzamide.

To carry out the method for detecting a soluble guanylate cyclase with a trivalent heme iron, it is possible to use chemical compounds which stimulate exclusively soluble guanylate cyclases with trivalent heme iron. It is likewise possible to use compounds which, besides activation of the soluble guanylate cyclase with a trivalent heme iron, also show other effects on the soluble guanylate cyclase. For example, it is possible to use chemical compounds which, besides activation of the soluble guanylate cyclase with a trivalent heme iron, also cause activation of the basal activity of the soluble guanylate cyclase or activation of the soluble guanylate cyclase with a divalent heme iron. A method for detecting soluble guanylate cyclase using chemical compounds which activate exclusively the enzyme form with trivalent heme iron or, for example, also enzyme forms with divalent heme iron is carried out with the assistance of reference values, calibration plots, and/or by comparison with substances which are able to activate exclusively a soluble guanylate cyclase with divalent heme iron (for example NO donors).

To construct a calibration plot, the soluble guanylate cyclase can be incubated with various concentrations of, for example, ODQ. The particular ratio of soluble guanylate cyclase with trivalent heme iron to soluble guanylate cyclase with divalent heme iron depends on the ODQ concentration employed in each case. The ODQ concentration used can be used directly as a measure of the proportion of enzyme with trivalent heme iron. The absolute proportion of soluble guanylate cyclase with trivalent heme iron can be checked for calibration purposes using other measurement methods, for example by ESR measurements. The soluble guanylate cyclases pretreated differently with ODQ are activated by the chemical compounds in an incubation step. In this, compounds which activate exclusively a soluble guanylate cyclase with trivalent heme iron give a value which is directly proportional to the amount of soluble guanylate cyclase with trivalent heme iron. Use of chemical compounds which, besides the soluble guanylate cyclase with trivalent heme iron, also activate the form with divalent heme iron, require an additional calibration plot with a substance which activates a soluble guanylate cyclase exclusively in the divalent form. The proportion of soluble guanylate cyclase with trivalent heme iron then emerges by comparing the activities obtained after different stimulation of a soluble guanylate cyclase pretreated with ODQ. For this, the soluble guanylate cyclase is stimulated once with a chemical compound which activates exclusively soluble guanylate cyclase with divalent heme iron and, on the other hand, a chemical compound which activates soluble guanylate cyclase with trivalent and divalent heme iron is used for the stimulation. Determination of the proportion of soluble guanylate cyclase with trivalent heme iron in a biological sample to be investigated results from comparison of the activity of the soluble guanylate cyclase from this sample after incubation with a chemical compound which is able to activate soluble guanylate cyclase as described above with the values in a calibration plot.

The provision of a chemical compound may also comprise dissolving this compound in a suitable solvent or solvents, such as, for example, dimethyl sulfoxide (DMSO) or water, and preparation of a formulation with auxiliary reagents.

The time for the incubation may vary in length, and various temperatures may be used. The time required and the temperature setting depend on the embodiments chosen in each case, considering the selection of the soluble guanylate cyclase provided, the chemical compound provided, and/or other conditions such as the preparation form, the concentration of the soluble guanylate cyclase employed and/or the chemical compound employed, and other additives. The incubation time can be, for example, between 1 minute and 120 minutes, a preferred incubation time is between 1 minute and 60 minutes, and a time of 30 minutes is particularly preferable. The temperature for the incubation can be between 5° C. and 45° C., and the temperature is preferably between 20° C. and 42° C. and, in the particularly preferred embodiment, the temperature is 37° C.

The detection of the activity of the soluble guanylate cyclase can take place, for example, by an enzyme assay, by a subsequent functional assay, or by a binding assay, for example in isolated cells or cell cultures. In a specific embodiment, this detection of the activity can take place by finding the inhibition of platelet aggregation using a Lumi-aggregometer. Platelets aggregate less after activation of the soluble guanylate cyclase and of the intracellular cGMP increase caused by the soluble guanylate cyclase. The extent of the inhibition of platelet aggregation is proportional to the activation of soluble guanylate cyclase and therefore provides a measure of the enzyme activation. In this embodiment of the invention, the soluble guanylate cyclase is not provided in isolated form, but is present in the platelet. The soluble guanylate cyclase can in principle also be used in this form for the methods of the present invention, i.e., where the cyclase is present in whole cells. In another preferred embodiment, the activity of soluble guanylate cyclase can also be measured by determining the cGMP formed using an RIA (radioimmunoassay) or EIA (enzyme immunoassay). In another preferred embodiment, the activity is determined via the effect of the chemical compounds on the cGMP formation in smooth muscle cells. Smooth muscle cells are a constituent of, for example, blood vessel walls. These muscle cells relax when the intracellular cGMP level increases. This may take place through activation of soluble guanylate cyclase. The relaxation of smooth muscle cells can therefore be used to detect activators of soluble guanylate cyclase.

The active pharmaceutical ingredients disclosed to date cannot activate a soluble guanylate cyclase when its heme iron is in the trivalent state. Chemical compounds able to activate soluble guanylate cyclase when its heme iron is oxidized in the tri-valent state have not previously been disclosed. Such chemical compounds could be used as active pharmaceutical ingredients in pharmaceuticals for stimulating soluble guanylate cyclase, for example in a pathological state caused by a soluble guanylate cyclase with a trivalent heme iron. It would likewise be possible to use such compounds in the method for detecting oxidized forms of soluble guanylate cyclase as described according to the invention. Another embodiment of the invention therefore relates to a method for finding a chemical compound which stimulates the activity of a soluble guanylate cyclase when the iron of the heme of the soluble guanylate cyclase is in the trivalent oxidation state, the method comprising:

a) provision of a soluble guanylate cyclase where the iron of the heme of this soluble guanylate cyclase is in the trivalent oxidation state;
   b) provision of at least one chemical compound to be investigated;
   c) incubation of a soluble guanylate cyclase according to a) with at least one chemical compound to be investigated, according to b); and
   d) determination of the activity of the soluble guanylate cyclase after incubation as in c).

Therefore, the instant invention encompasses a method for identifying a chemical compound which stimulates the activity of soluble guanylate cyclase having a heme group with iron in a trivalent oxidation state, comprising:

a) incubating a sample of soluble guanylate cyclase having a known activity and having a heme group with iron in the trivalent oxidation state with a test chemical compound;
   b) measuring the activity of soluble guanylate cyclase after incubation; and
   c) comparing the activity of the soluble guanylate cyclase after incubation with the activity before incubation, wherein an increase in activity indicates the chemical compound stimulates the activity of the soluble guanylate cyclase having a heme group with iron in the trivalent oxidation state.

A method for finding a chemical compound is also referred to as screening. The use and provision of the soluble guanylate cyclase for the screening method takes place as already stated for the method for detecting a soluble guanylate cyclase with trivalent heme iron.

The provision of the soluble guanylate cyclase for the screening may include the preparation of suitable forms for the incubation with a chemical compound to be investigated. The soluble guanylate cyclase can, for example, be suspended or dissolved in aqueous solvents supplemented by buffers, ions, and/or auxiliary reagents. It can also be attached to carrier material and can be used immobilized in this form suspended in solvents.

The chemical compound to be investigated in the screening may be a chemically synthesized compound, or a natural product, or a combination thereof. The chemical compound to be investigated may be present in various states of matter, for example, as a single substance in purified form, as mixture with other compounds which need not be characterized in detail, as mixture of various active compounds, as constituent of a mixture of compounds of biological origin, or together with eukaryotic and/or prokaryotic organisms.

The screening method can be carried out, for example, by a laboratory robot or with the assistance of machines. Chemical compounds to be investigated, which activate a soluble guanylate cyclase with a trivalent heme iron, may be used as active pharmaceutical ingredients for treating conditions with pathological changes, such as, for example, cancer, angina pectoris, diabetes, myocardial infarct, erectile dysfunction, heart failure, high blood pressure, thromboses, anemia, or vascular dysfunction. The invention also relates to the chemical compound to be investigated which is identified by this screening method as activator of a soluble guanylate cyclase whose heme iron is in the trivalent oxidation state.

The invention relates very generally to compounds which are able to activate the activity of a soluble guanylate cyclase whose heme iron is in the trivalent oxidation state, and to the use of these substances, preferably as active pharmaceutical ingredients. The invention accordingly also relates to compounds which are able to activate a soluble guanylate cyclase whose heme iron is in the trivalent oxidation state, and which can therefore be employed as active pharmaceutical ingredients for the treatment or prevention of pathological states caused by or intensified by soluble guanylate cyclase with heme iron in the trivalent oxidation state. Such pathological states may include, for example, cancer, angina pectoris, diabetes, myocardial infarct, erectile dysfunction, heart failure, high blood pressure, thromboses, vascular dysfunction, or anemia.

The invention also relates to a diagnostic aid or kit for carrying out a method for determining the oxidation state of heme iron in a soluble guanylate cyclase. The diagnostic aid can for this purpose comprise at least one or more of the following components: a) at least one chemical compound which stimulates the activity of soluble guanylate cyclase when the heme iron of this soluble guanylate cyclase is in the trivalent oxidation state, and b) solutions and/or reagents for determining the activity of a soluble guanylate cyclase. An example of a chemical compound which can be used in the diagnostic aid or kit is 2-(4-chlorophenylsulfonylamino)-4,5-dimethoxy-N-(4-(thiomorpholine-4-sulfonyl)phenyl)benzamide. The activity can be determined by one of the methods already described above.

The diagnostic aid may also comprise, for example, soluble guanylate cyclase, a chemical compound which activates a soluble guanylate cyclase only when the heme iron is in the divalent state, an oxidizing agent, and/or ODQ. These constituents can be used singly or in combination to establish a reference value or a calibration plot for quantitative or qualitative determination of soluble guanylate cyclase with a heme iron in the trivalent oxidation state.

The diagnostic aid may be used, for example, for determining the content of soluble guanylate cyclase with trivalent heme iron in a biological sample. A biological sample might consist, for example, of cells from a tissue or organ of a vertebrate or of a human. These cells might have been taken from an organism or have been grown by cell culturing techniques. The donor organisms which may be selected are individuals with tissues or organs which are healthy or show pathological changes. For example, organ samples, tissue samples, blood samples, cells or biopsy material can be taken using medical techniques from human or animal organisms and serve as biological sample. It is also possible to carry out comparative analysis of the biological samples from different individuals in connection with the oxidation state of the heme iron in the soluble guanylate cyclase in the light of their different living and eating habits. Thus, for example, the cells of smokers and nonsmokers could be obtained and analyzed. The soluble guanylate cyclases of the smokers could be compared with those of nonsmokers for differences in the ratio of divalent heme iron to trivalent heme iron.

The invention relates in a preferred embodiment to an in vitro method for determining the oxidation state of the heme iron in a soluble guanylate cyclase in a biological sample which has been taken from a eukaryotic organism. The biological sample taken from a eukaryotic organism may contain, for example, healthy or pathologically changed cells from cell cultures, tissues, or organs.

In another preferred embodiment, a diagnostic aid described according to the invention can be used to carry out the in vitro method. Examples of possible biological states with pathological changes are cancer, angina pectoris, diabetes, erectile dysfunction, myocardial infarct, heart failure, high blood pressure, thromboses, anemia, vascular dysfunction, and others. It is also possible to investigate certain living or eating habits such as, for example, smoking or alcohol consumption for the effects on the oxidation state of heme iron in the soluble guanylate cyclase.

In healthy biological states, the parameters used for the characterization fall within the normal range. Appropriate information for establishing the normal ranges is to be found, for example, in textbooks of clinical chemistry (for example *Clinical Chemistry, Principles, Procedures, Correlations,* Michael L. Bishop and Janet L. Duben-Enkelkirk, Eds., Lippincott, Williams & Williams).

The invention also relates to a method for detecting a soluble guanylate cyclase using a luminometric assay. The assay comprises several steps, carried out successively or simultaneously. The luminometric assay comprises the following steps: a) provision of a soluble guanylate cyclase and GTP as substrate, b) conversion of the GTP by the provided soluble guanylate cyclase to form cGMP and pyrophosphate, c) provision of a nicotinamide mononucleotide adenyltransferase and nicotinamide dinucleotide ($NAD^+$), d) conversion of the pyrophosphate formed in b) by the nicotinamide mononucleotide adenyltransferase in the presence of nicotinamide dinucleotide ($NAD^+$) to form ATP, e) provision of a luciferase and its substrate luciferin, and f) luminometric determination of the formed ATP by reaction with luciferin under luciferase catalysis. The amount of formed ATP is proportional to the concentration of soluble guanylate cyclase. The method is started by adding soluble guanylate cyclase to a reaction mixture which, besides other substances, contains GTP as substrate. Other substances present can be, for example, buffers, ions, or proteins.

The method for detecting the soluble guanylate cyclase is suitable in a preferred embodiment for carrying out a screening of chemical compounds to be investigated for their suitability for stimulating the activity of soluble guanylate cyclase. The advantage of this luminometric method compared with methods previously used for detecting soluble guanylate cyclase (i.e., immunological, enzymatic, or photometric methods) lies in the ability to screen large quantities of chemical compounds for their potential ability to stimulate the activity of a soluble guanylate cyclase with trivalent heme iron in considerably shorter times. To carry out the screening, the chemical compound to be investigated is added to the reaction mixture before the start of the method by addition of soluble guanylate cyclase. The method is suitable in a particular embodiment of the screening for use in a laboratory robot, and in another particularly preferred embodiment for manual performance. The provision of the soluble guanylate cyclase can take place as already stated in the previous sections for the soluble guanylate cyclase. A particular advantage of this luminometric assay is that the components for carrying out the method, such as GTP, nicotinamide mononucleotide adenyltransferase, $NAD^+$, luciferin or luciferase, can be provided in a reaction vessel. The activity of soluble guanylate cyclase is established by determining the amount of ATP formed. The reaction is started by adding soluble guanylate cyclase. This makes it possible to carry out the method in a one-pot reaction. This can also be applied to screening with high throughput of chemical substances to be investigated (high throughput screening; HTS) and can be carried out reproducibly. This luminometric assay is very suitable in particular for detecting small amounts of pyrophosphate. The method can in a preferred embodiment be used to determine the activity of a soluble guanylate cyclase. The luminometric assay is also suitable for carrying out a method as described in the preceding sections for detecting soluble guanylate cyclase with trivalent heme iron.

The invention also relates to a method for detecting a soluble guanylate cyclase where the soluble guanylate cyclase has no heme group. The method comprises: a) provision of a soluble guanylate cyclase without a heme group, b) provision of at least one chemical compound able to stimulate the activity of soluble guanylate cyclase when the soluble guanylate cyclase has no heme group, c) incubation of a soluble guanylate cyclase with a chemical compound able to stimulate the activity of a soluble guanylate cyclase without a heme group and d) determination of the activity of the soluble guanylate cyclase without a heme group after incubation with the chemical compound.

The invention also relates to a method for finding a chemical compound which stimulates the activity of a soluble guanylate cyclase where the soluble guanylate cyclase has no heme group. This method can comprise as steps a) provision of a soluble guanylate cyclase which has no heme group, b) provision of at least one chemical compound to be investigated, c) incubation of a soluble guanylate cyclase without heme group with at least one chemical compound to be investigated, and d) determination of the activity of the soluble guanylate cyclase after incubation.

The invention also relates to a diagnostic aid for determining the oxidation state of a soluble guanylate cyclase without a heme group, comprising at least one chemical compound which stimulates the activity of a soluble guanylate cyclase where the soluble guanylate cyclase has no heme group. The invention also relates to an in vitro method for determining a soluble guanylate cyclase which has no heme group in a biological sample, where the method may comprise as steps the provision of a biological sample which contains a soluble guanylate cyclase without heme group, the provision of at least one chemical compound able to stimulate the activity of a soluble guanylate cyclase without a heme group, the incubation of a soluble guanylate cyclase without heme group with a chemical compound able to stimulate the activity of a soluble guanylate cyclase, and the determination of the activity of the soluble guanylate cyclase without heme group after incubation with the chemical compound. A method for provision of a soluble guanylate cyclase without a heme group is described in Foerster, J. et al., *Eur. J. Biochem.* 240, 380–386 (1996). An example of a suitable chemical compound for stimulating a soluble guanylate cyclase without a heme group is the chemical compound 2-(4-chlorophenylsulfonylamino)-4,5-dimethoxy-N-(4-thiomorpholine-4-sulfonyl)phenyl)benzamide.

EXAMPLES

Example 1

Luminometric Method for Detecting the Activity of Soluble Guanylate Cyclase

Soluble guanylate cyclase (sGC) catalyzes the conversion of GTP into cGMP and pyrophosphate. In the presence of nicotinamide adenine dinucleotide ($NAD^+$) and nicotinamide mononucleotide adenylyltransferase (NAT, EC 2.7.7.1), pyrophosphate is converted into ATP and nicotinamide mononucleotide. The ATP formed can be quantified luminometrically with the aid of a luciferase in microtiter plates.

The substance to be investigated is dissolved in DMSO and diluted with DMSO/water to a final concentration of 50 µM in the assay mixture. The DMSO concentration in the assay mixture should not exceed 5% (v/v).

100 µl of reaction mixture should contain 50 mM TEA buffer (pH 7.4), 3 mM $MgCl_2$, 3 mM GSH, 0.1 mM GTP, 1 mM IBMX (isobutylmethylxanthine), 0.2 mM $NAD^+$, 0.4 mU of NAT, suitably diluted sGC enzyme solution (isolated from bovine lung as described by P. Humbert et al., *Methods of Enzymology* 195, 384–391 (1991)) and the test substance or solvent (for determining the basal enzyme activity). The reaction is started by adding the sGC. The reaction mixture is incubated at room temperature for 60 min and then stopped by cooling in ice and adding 50 mM EDTA, pH 8.0. For the ATP determination, 20 µl of 100 mM $MgCl_2$ and 50 µl of ATP assay reagent (0.035 mM luciferin and 10,000 U/mL luciferase in 62.5 mM TRIS acetate pH 7.75, 1.9 mM EDTA, 0.05 mM DTT, 0.1% BSA) are added. The relative luminescence units (RLU) can be measured in a microtiter plate luminometer.

The sGC activity is obtained after subtracting the blank RLU (incubation without enzyme) from the measured RLU. Activation of the sGC by a test substance is indicated as a percentage of the basal enzyme activity (solvent control) and is calculated by the following formula:

$$100\times(DRLU_{test\ substance}/DRLU_{control})-100=\%\ activation$$

Example 2

Activation of Soluble Guanylate Cyclase after Oxidation of the Heme Iron

Isolated sGC is present in solution in a heme $Fe^{2+}$-containing (reduced) form which can be stimulated by NO and a heme $Fe^{3+}$-containing (oxidized) form which cannot be stimulated by NO. The proportion of each form previously was determined only by ESR measurements.

Nitric oxide (NO) and NO donors activate exclusively the reduced state of sGC. On incubation in the presence of, for example, 0.01 mM 1H-[1,2,4]oxadiazolo[4,3-a]quinoxalin-1-one (ODQ), which irreversibly oxidizes sGC in vitro, they show complete loss of their stimulating effect. A novel NO-independent activator of sGC, 1-benzyl-3-(2-hydroxymethyl-5-furyl)indazole (YC-1), likewise activates the reduced form of sGC and can be inhibited by ODQ.

In contrast, stimulation by substances which activate exclusively or predominantly the oxidized form is either enhanced or unaffected by ODQ, depending on the proportion of the oxidized form in the mixture.

These substances likewise frequently show an activation of the heme-free form of sGC. The preparation of a heme-free sGC is carried out according to J. Foerster et al., *Eur. J. Biochem.* 240, 380–386 (1996).

A soluble guanylate cyclase with a trivalent heme iron was prepared by storing freshly prepared enzyme at 4° C. for about 7 days. Incubation of soluble guanylate cyclase pretreated in this way with 2-(4-chlorophenylsulfonylamino)-4,5-dimethoxy-N-(4-(thiomorpholine-4-sulfonyl)phenyl) benzamide resulted in 17.6-fold stimulation of the activity. The EC50 was 0.5 µmol/l. The stimulation on use of a heme-free soluble guanylate cyclase reached 58.2-fold. The affinity in this case was 2.4 µmol/l.

Example 3

Detection of the Stimulation of Soluble Guanylate Cyclase after Oxidation of the Heme Iron by Determining the Effect on Platelet Aggregation The physiological effect of nitric oxide (NO) such as inhibition of platelet aggregation and relaxation of smooth vascular muscles is the consequence of direct activation of soluble (reduced) guanylate cyclase by NO with increased formation of cGMP.

ODQ, a selective sGC inhibitor, inhibited, through oxidation of the sGC, the increase in cGMP and the antiaggregatory effect of NO donors in washed human platelets (M. A. Moro et al., *PNAS* 93, 1480–1485 (1996)).

To prepare washed human platelets (WP), blood is taken from the antecubital vein and anticoagulated in the syringe with citric acid/sodium citrate. After centrifugation at 16×g for 15 min, the supernatant consists of platelet-rich plasma (PRP). The PRP is acidified, and the platelets are sedimented by centrifugation at 400×g for 20 min and taken up in Tyrode solution. These washed platelets (WP, $3\times10^5/\mu L$) are employed in the tests.

The inhibition of aggregation by sGC activators is determined in a Lumiaggregometer. The WPs are incubated with the test substance in the presence of 0.5 mM $CaCl_2$ at 37° C., and the reaction is started by adding, for example, 0.3 µg/mL collagen. The effect of the substances on aggregation is investigated in the absence and presence of ODQ. sGC activators will show dose-dependent inhibition of collagen-induced platelet aggregation. Activators which stimulate the oxidized form of sGC will show a stronger antiaggregatory effect in the presence of ODQ. The $IC_{50}$ for the inhibition of aggregation will be shifted to lower concentrations.

To determine the intracellular cGMP concentration, WPs are incubated in the presence of 0.1 mM isobutylmethylxanthine (IBMX) at 37° C. for 15 min. The incubation is stopped by centrifugation, and the precipitate is treated with 1M perchloric acid and ultrasound for 1 min. After renewed centrifugation at 13,000×g for 15 min, the supernatant is neutralized with 1M KOH, and the cGMP concentration is determined using a commercial enzyme immunoassay (available from Amersham, inter alia) for cGMP. The protein concentration in the precipitate is determined by the Bradford method.

Chemical compounds which activate the activity of soluble guanylate cyclase will lead to a concentration-dependent increase in the intracellular cGMP concentration. If the incubation is carried out in the presence of ODQ, it should be possible to obtain significantly higher cGMP levels than without ODQ using chemical compounds which stimulate the activity of soluble guanylate cyclase with trivalent heme iron, i.e., ODQ should enhance the effect of the substances.

Example 4

Detection of the Stimulation of Soluble Guanylate Cyclase after Oxidation of the Heme Iron by Determining the Effect on Smooth Muscle Cells from Rat Aorta Smooth muscle cells (VSMC) from rat aorta are isolated and cultivated by the method of J. H. Chamley et al., *Cell Tissue Res.* 177, 503–522 (1977).

The cells are seeded in 6-well plates and incubated in HEPES-Tyrode buffer (pH 7.4 with 200 U SOD, 0.3 mM IBMX) at 37° C. for 15 min. The effect of the substances on the VSMC is investigated in the absence and presence of ODQ. The incubation is stopped by aspirating off the supernatant and adding liquid nitrogen, and the cells are deep-frozen in the 6-well plates. To determine cGMP, the plates are thawed, the individual wells are charged with buffer, and the cGMP concentration in the supernatant is determined with a commercial enzyme immunoassay (available from Amersham, inter alia) for cGMP. The protein concentration is determined by the Bradford method after the protein in the wells has been dissolved with 0.1 M NaOH.

Chemical compounds which stimulate the activity of soluble guanylate cyclase will lead to a concentration-dependent increase in the intracellular cGMP concentration. If the incubation is carried out in the presence of ODQ considerably higher cGMP levels will be obtained with chemical compounds which stimulate the activity of soluble guanylate cyclase with a trivalent heme iron. ODQ ought to enhance the effect of the activating compounds.

Example 5

Preparation of 2-(4-chlorophenylsulfonylamino)-4, 5-dimethoxy-N-(4-(thiomorpholine-4-sulfonyl) phenyl)benzamide 33.71 g (0.32 mol) of sodium carbonate were dissolved in 250 ml of water and heated to 60° C. 25.00 g (0.13 mol) of 2-amino-4,5-dimethoxybenzoic acid were introduced into the solution, and 29.55 g (0.14 mol) of 4-chlorobenzenesulfonyl chloride were added in portions to this solution over the course of 15 min. After the mixture had been cooled, the residue was filtered off with suction and taken up in 1% strength sodium bicarbonate solution and, after filtration, the product was precipitated by adding 1 N hydrochloric acid. 25.90 g (55%) of 2-(4-chlorophenylsulfonylamino)-4,5-dimethoxybenzoic acid of melting point 212–214° C. were obtained. 25.90 g (0.07 mol) of 2-(4-chlorophenylsulfonylamino)-4,5-dimethoxybenzoic acid were suspended in 75 ml of toluene and, after addition of 17.30 g (0.08 mol) of phosphorus pentachloride, the mixture was stirred at 40–45° C. for 2.5 h. It was then concentrated to half the volume in vacuo, and the precipitated product was filtered off with suction and washed with a little toluene. 25.30 g (93%) of 2-(4-chlorophenylsulfonylamino)-4,5-dimethoxybenzoyl chloride, of melting point 175–177° C., were obtained.

10.00 g (25.6 mmol) of 2-(4-chlorophenylsulfonylamino)-4,5-dimethoxybenzoyl chloride were suspended in 300 ml of toluene, 4.49 g (25.6 mmol) of 4-aminobenzenesulfonyl fluoride were added, and the mixture was heated under reflux for 4 h. After cooling, the precipitate which had separated out was filtered off with suction and washed with toluene. 11.71 g (87%) of the title compound, of melting point 216–219° C., were obtained.

500 mg (0.95 mmol) of 4-((2-(4-chlorophenylsulfonylamino)-4,5-dimethoxybenzoyl)amino) benzenesulfonyl fluoride were dissolved in 1 ml of thiomorpholine and heated at 90° C. for 30 min. For workup, the mixture was poured into 50 ml of ice/1 N hydrochloric acid, and the precipitate was filtered off with suction, dried in a vacuum dryer over phosphorus pentoxide, and recrystallized from hexane/ethyl acetate. 378 mg (65%) of the title compound of melting point 241° C. were obtained.

The present invention may be embodied in other specific forms without departing from its spirit or essential characteristics. The described embodiments are to be considered in all respects as illustrative only and not restrictive. The scope of the invention is, therefore, indicated by the appended claims rather than by the foregoing description. All changes which come within the meaning and range of equivalency of the claims are to be embraced within their scope.

We claim:

1. A method for detecting soluble guanylate cyclase having a heme group with iron in a trivalent oxidation state, comprising:

a) incubating a sample of soluble guanylate cyclase having a known activity with a chemical compound which stimulates activity of soluble guanyl ate cyclase having a heme group with iron in the trivalent oxidation state;

b) measuring the activity of the soluble guanylate cyclase after incubation; and c) comparing the activity of the soluble guanylate cyclase after incubation with the activity before incubation, wherein an increase in activity indicates the presence of soluble guanylate cyclase having a heme group with iron in the trivalent oxidation state.

2. The method as claimed in claim 1, wherein the sample of soluble guanylate cyclase is from a mammal.

3. The method as claimed in claim 2, wherein the sample of soluble guanylate cyclase is from cattle.

4. The method as claimed in claim 2, wherein the sample of soluble guanylate cyclase is from a human.

5. The method as claimed in claim 1, wherein the sample of soluble guanylate cyclase comprises an $\alpha$ subunit and a $\beta$ subunit, wherein the $\alpha$ subunit is an $\alpha_1$ or $\alpha_2$ subunit and the $\beta$ subunit is a $\beta_1$ or $\beta_2$ subunit.

6. The method as claimed in claim 1, wherein the sample of soluble guanylate cyclase is isolated from a biological material.

7. The method as claimed in claim 1, wherein the activity of the soluble guanylate cyclase is determined by a functional assay or a binding assay.

8. The method as claimed in claim 1, wherein the sample of soluble guanylate cyclase is treated with an oxidizing agent.

9. The method as claimed in claim 8, wherein the sample of soluble guanylate cyclase is treated with 1H-(1,2,4) oxadiazolo(4,3-a)quinoxalin-1-one.

10. The method as claimed in claim 8, wherein the sample of soluble guanylate cyclase is treated with oxadiazolo(3,4-d)benz(b)(1,4)oxazin-1-one.

11. The method as claimed in claim 8, wherein the sample of soluble guanylate cyclase is treated with potassium ferricyanide.

12. A method for detecting soluble guanylate cyclase lacking a heme group, comprising:

a) incubating a sample of soluble guanylate cyclase having a known activity with a chemical compound which stimulates the activity of a soluble guanylate cyclase lacking a heme group;

b) measuring the activity of the sample after incubation; and c) comparing the activity of the sample after incubation with the activity before incubation, wherein an increase in activity indicates the presence of the soluble guanylate cyclase lacking a heme group.

* * * * *

UNITED STATES PATENT AND TRADEMARK OFFICE
CERTIFICATE OF CORRECTION

PATENT NO. : 6,500,631 B1
DATED : December 31, 2002
INVENTOR(S) : Schindler et al.

It is certified that error appears in the above-identified patent and that said Letters Patent is hereby corrected as shown below:

Title page,
Item [57], ABSTRACT,
Line 8, after "relates", insert -- to --.

Column 14,
Line 16, "guanyl ate" should read -- guanylate --.

Signed and Sealed this

Thirteenth Day of May, 2003

JAMES E. ROGAN
*Director of the United States Patent and Trademark Office*